United States Patent [19]

Bittler et al.

[11] Patent Number: 4,464,364

[45] Date of Patent: Aug. 7, 1984

[54] 6β,7β-METHYLENE-17α-PREGN-4-ENE-21,17-CARBOLACTONES, THEIR PREPARATION AND USE AS MEDICINAL AGENTS

[75] Inventors: Dieter Bittler; Henry Laurent; Rudolf Weichert, all of Berlin; Jorge Casals-Stenzel, Mainz; Ekkehard Schillinger, Berlin, all of Fed. Rep. of Germany

[73] Assignee: Schering Aktiengesellschaft, Berlin & Bergkamen, Fed. Rep. of Germany

[21] Appl. No.: 502,848

[22] Filed: Jun. 9, 1983

[30] Foreign Application Priority Data

Jun. 9, 1982 [DE] Fed. Rep. of Germany ....... 3222265

[51] Int. Cl.³ ............................................. A61K 31/33
[52] U.S. Cl. ................................. 424/241; 260/239.57
[58] Field of Search .................................... 260/239.57

[56] References Cited

U.S. PATENT DOCUMENTS 4,291,029 9/1981 Wiechert et al. .............. 260/239.57

Primary Examiner—Elbert L. Roberts
Attorney, Agent, or Firm—Millen & White

[57] ABSTRACT

Novel 6β,7β-methylene-17α-pregn-4-ene-21,17-carbolactones of Formula I

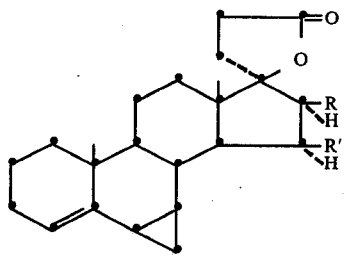

wherein
R and R' each is hydrogen or jointly form a methylene group.

These exhibit a good antimineralocorticoid effect with low side effects.

10 Claims, No Drawings

6β,7β-METHYLENE-17α-PREGN-4-ENE-21,17-CARBOLACTONES, THEIR PREPARATION AND USE AS MEDICINAL AGENTS

The present invention relates to new compounds having valuable pharmacological properties.

It is an object of this invention to provide such new compounds.

Upon further study of the specification and appended claims, further objects and advantages of this invention will become apparent to those skilled in the art.

These objects have been achieved by providing novel 6β,7β-methylene-17α-pregn-4-ene-21,17-carbolactones of Formula I

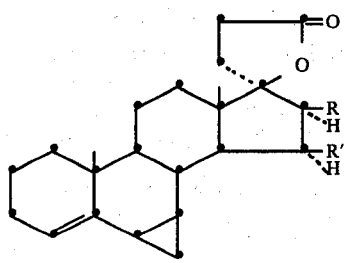

wherein
R and R' each is hydrogen or jointly form a methylene group.

These exhibit a good antimineralocorticoid effect with low side effects.

DETAILED DISCUSSION

This invention furthermore concerns a process for the preparation of the 6β,7β-methylene-17α-pregn-4-ene-21,17-carbolactones of this invention, e.g., by conventionally reducing the corresponding 6β,7β-methylene-3-oxo-17α-preg-4-ene-21,17-carbolactones of the formula II

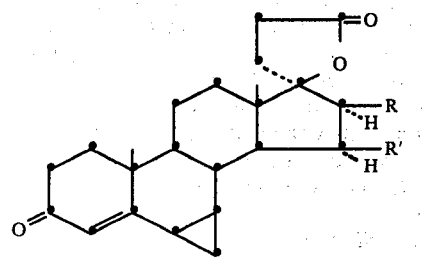

wherein
R and R' are as defined above.

The starting compounds are known or readily preparable using fully conventional methods.

The reduction of the 3-keto group in conjugation with the Δ⁴-double bond takes place in a manner known per se (See, e.g., A. J. van den Broek et al, Recueil, J. Royal Netherlands Chem. Soc. 94:35 [1975] whose disclosure is incorporated by reference herein.), after thioketalization, for example with lithium in liquid ammonia, with Raney nickel in a protonic solvent, such as methanol, or with hydrogen in the presence of a noble metal catalyst on a suitable support material. In order to conduct the process, the Δ⁴-3-keto steroid carbolactone can be reacted in methanol with ethanedithiol in the presence of condensation agents to obtain the 3,3-ethylenedithioketal. Suitable condensation agents include sodium sulfate/zinc chloride or boron trifluoride etherate.

If the reductive splitting of the 3,3-ethylenedithioketal is effected with lithium, the starting material can be dissolved, for example, in tetrahydrofuran and added to a solution of lithium in ammonia. If the reduction is carried out with hydrogen in the presence of a noble metal catalyst, such as palladium on charcoal or palladium on calcium carbonate, hydrogenation is continued until somewhat more than 1 molar equivalent of hydrogen has been absorbed. Reduction with Raney nickel in methanol is preferred, since it is easy to conduct technically. The starting material, dissolved in methanol/tetrahydrofuran, is usually combined with the catalyst at room temperature; the catalyst is subsequently removed again by filtration. The reaction mixture is then worked up conventionally such as by precipitation, extraction, recrystallization and/or chromatography.

The compounds of this invention possess valuable pharmacological properties. They are, inter alia, diuretics of the the type of the aldosterone antagonists, i.e., they reverse the effect of deoxycorticosterone on the excretion of sodium and postassium. They show good antimineralocorticoid effects and have low side effects.

The compounds of this invention surprisingly prove to be superior in efficacy over the conventional spironolactone in a test model according to Hollmann (G. Hollmann et al., "Tubulaere Wirkungen und renale Elimination von Spirolactonen" [Tubular Effects and Renal Elimination of Spirolactones], Naunyn-Schmiedebergs Arch. Exp. Path. Pharmak. 247:419 [1964]; P. Marx, "Renale Wirkungen des d-Aldosterons und seines Antagonisten Spironolacton" [Renal Effects of d-Aldosterone and Its Antagonist Spironolactone], Diss. Med. Fak. FU Berlin, 1966).

The compounds of this invention can be utilized by means of conventional methods of galenic pharmacy for the production of medicinal agents for oral and parenteral administration, e.g., to mammals, including humans. Oral administration is preferred.

The dosage of the compound of this invention in human patients is usually about 5–100 mg/day. The unit dosage form, such as tablets, dragees, capsules, and similar forms, usually has a content of active agent of 5–50 mg.

Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or implants, including suppositories. Ampoules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Dosages for a given host for a given indication can be determined, e.g., by customary comparison of the activities of the subject compound and of a known agent by means of an appropriate, conventional pharmacological protocol. Such a known agent is spironolactone, to whose administration that of this invention is generally analogous.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(A) Under ice cooling, a solution of 2.5 g of 6β,7β;15β,16β-dimethylene-3-oxo-17α-pregn-4-ene-21,17-carbolactone in 50 ml of methanol is combined with 2.5 ml of ethanedithiol, 2.5 g of sodium sulfate, and 1.25 g of molten zinc chloride and stirred for one hour. The reaction solution is diluted with diethyl ether, washed neutral with sodium hydroxide solution and water, dried, and evaporated. The crude product is chromatographed on silica gel with an acetone-hexane gradient, thus obtaining 1.65 g of 3,3-ethylenedithio-6β,7β;15β,16β-dimethylene-17α-pregn-4-ene-21,17-carbolactone, mp 266.4° C. (from diisopropyl ether).

(B) 750 mg of 3,3-ethylenedithio-6β,7β;15β,16β-dimethylene-17α-pregn-4-ene-21,17-carbolactone, dissolved in 8 ml of tetrahydrofuran, is added to a solution of 100 mg of lithium in ammonia, cooled to −75° C. The mixture is agitated for 1.5 hours under cooling; then the reaction vessel is heated in a water bath, and the ammonia is evaporated. The residue is dissolved in diethyl ether, the solution is washed with dilute sulfuric acid and water, dried, and evaporated. The residue is chromatographed on silica gel with an acetone-hexane gradient. The thus-obtained product is crystallized from diisopropyl ether, yielding 320 mg of 6β,7β;15β,16β-dimethylene-17α-pregn-4-ene-21,17-carbolactone, mp 188.7° C.

EXAMPLE 2

A solution of 200 mg of 3,3-ethylenedithio-6β,7β;15β,16β-dimethylene-17α-pregn-4-ene-21,17-carbolactone in a mixture of 3 ml of methanol and 1 ml of tetrahydrofuran is combined with 1 g of Raney nickel and stirred for one hour at room temperature. Subsequently the mixture is filtered off from Raney nickel and washed with dichloromethane. The combined solutions are washed with water, dried, and evaporated. The residue is purified by preparative layer chromatography on silica gel. After recrystallization from diisopropyl ether, 54 mg of 6β,7β;15β,16β-dimethylene-17α-pregn-4-ene-21,17-carbolactone is obtained, mp 186.5° C.

EXAMPLE 3

5.5 g of 6β,7β;15β,16β-dimethylene-3-oxo-17α-pregn-4-ene-21,17-carbolactone is hydrogenated in a mixture of 55 ml of tetrahydrofuran and 55 ml of propan-2-ol in the presence of 550 mg of palladium-charcoal catalyst until 1.4 equivalents of hydrogen has been absorbed. After removing the catalyst by filtration, the filtrate is evaporated and the resultant residue is chromatographed on silica gel. Yield: 710 mg of 6β,7η;15β,16β-dimethylene-17α-pregn-4-ene-21,17-carbolactone, mp 184.5° C. (from diisopropyl ether).

EXAMPLE 4

(A) A solution of 1.0 g of 6β,7β-methylene-3-oxo-17α-pregn-4-ene-21,17-carbolactone in a mixture of 5 ml of tetrahydrofuran and 5 ml of methanol is combined with 1 ml of ethanedithiol and 0.4 ml of boron trifluoride etherate; the mixture is stirred for 1.5 hours at room temperature. The reaction solution is diluted with dichloromethane, washed with dilute sodium hydroxide solution and water, dried, and evaporated. The residue becomes crystalline when treated with diisopropyl ether.

Yield: 1.15 g of 3,3-ethylenedithio-6β,7β-methylene-17α-pregn-4-ene-21,17-carbolactone, mp 237.6° C.

(B) 600 mg of 3,3-ethylenedithio-6β,7β-methylene-17α-pregn-4-ene-21,17-carbolactone is dissolved in a mixture of 4 ml of methanol and 4 ml of tetrahydrofuran; the solution is combined with 3 g of Raney nickel and stirred for 18 hours at room temperature. The working-up process is conducted as described in Example 2, including chromatography, thus obtaining 230 mg of 6β,7β-methylene-17α-pregn-4-ene-21,17-carbolactone as an oil.

$[\alpha]_D^{23} = -57°$ (in chloroform).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 6β,7β-methylene-17α-pregn-4-ene-21,17-carbolactone of the formula

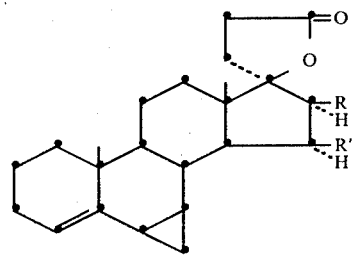

wherein
R and R' each is hydrogen or together form a methylene group.

2. A compound of claim 1 wherein R and R' are H.

3. A compound of claim 1 wherein R and R' form a methylene group.

4. A pharmaceutical composition comprising a diuretically effective amount of a compound of claim 1 and a pharmaceutically acceptable carrier.

5. A pharmaceutical composition of claim 4 wherein the amount of said diuretically effective compound is 5–50 mg.

6. A pharmaceutical composition of claim 4 wherein in the said active agent, R and R' are each H.

7. A pharmaceutical composition of claim 4 wherein in said active agent, R and R' together form methylene.

8. A method of achieving a diuretic effect in a patient in need of such treatment comprising administering to the patient an amount of a compound of claim 1 effective as a diuretic.

9. A method of claim 8 wherein in said active agent, R and R' are each H.

10. A method of claim 8 wherein in said active agent, R and R' together form methylene.

* * * * *